(12) United States Patent
Curtis

(10) Patent No.: US 11,167,145 B2
(45) Date of Patent: Nov. 9, 2021

(54) SYSTEM AND METHOD FOR INDIRECT MEASUREMENT OF VENTRICULAR CONTRACTILITY

(71) Applicant: Guy P. Curtis, San Diego, CA (US)

(72) Inventor: Guy P. Curtis, San Diego, CA (US)

(73) Assignee: Guy P. Curtis and Frances L. Curtis Trust, San Diego, CA (US)

( * ) Notice: Subject to any disclaimer, the term of this patent is extended or adjusted under 35 U.S.C. 154(b) by 104 days.

(21) Appl. No.: 16/668,971

(22) Filed: Oct. 30, 2019

(65) Prior Publication Data

US 2021/0128924 A1 May 6, 2021

(51) Int. Cl.
*A61N 1/365* (2006.01)

(52) U.S. Cl.
CPC ..... *A61N 1/36564* (2013.01); *A61N 1/36585* (2013.01)

(58) Field of Classification Search
None
See application file for complete search history.

(56) References Cited

U.S. PATENT DOCUMENTS

| | | | |
|---|---|---|---|
| 3,412,729 A | 11/1968 | Smith | |
| 3,556,084 A * | 1/1971 | Budde | A61B 5/02255 600/479 |
| 4,479,494 A | 10/1984 | McEwen | |
| 4,860,759 A | 8/1989 | Kahn | |
| 4,951,679 A | 8/1990 | Harada | |
| 5,423,746 A | 6/1995 | Burkett | |
| 5,772,601 A | 6/1998 | Oka | |
| 5,776,071 A | 7/1998 | Inukai | |
| 6,511,413 B2 | 1/2003 | Landesberg | |
| 6,527,725 B1 | 3/2003 | Inukai | |
| 6,547,742 B2 | 4/2003 | Oka | |
| 7,300,404 B1 | 11/2007 | Kolluri | |
| 7,336,997 B2 | 2/2008 | Fukui | |
| 7,653,440 B1 * | 1/2010 | Bornzin | A61N 1/36114 607/116 |
| 8,463,376 B2 | 6/2013 | Curtis | |
| 2005/0177046 A1 * | 8/2005 | Mills | A61B 5/0285 600/481 |
| 2009/0043349 A1 * | 2/2009 | Wang | A61N 1/3684 607/23 |
| 2011/0004264 A1 * | 1/2011 | Siejko | A61N 1/368 607/28 |
| 2016/0310740 A1 | 10/2016 | Curtis | |

OTHER PUBLICATIONS

Extended European Search Report; European Patent Application No. 20202812.2; dated Apr. 14, 2021.

* cited by examiner

*Primary Examiner* — Brian T Gedeon
(74) *Attorney, Agent, or Firm* — Neil K. Nydegger

(57) ABSTRACT

A system for monitoring and evaluating the ventricular contractility of a heart muscle includes a device for electrically stimulating the heart muscle of a patient, and an extracorporeal blood pressure sensor. A record, responsive to stimulated ventricular contractions, is created by the pressure sensor. The response record is then evaluated to identify a pressure/time, rate-change in arterial pressure (dp/dt) that results within the time duration of a ventricular contraction in a cardiac cycle. In turn, dp/dt is evaluated as an indicator of ventricular contractility and the health of the patient's heart muscle.

15 Claims, 2 Drawing Sheets

SYSTEM AND METHOD FOR INDIRECT MEASUREMENT OF VENTRICULAR CONTRACTILITY

FIELD OF THE INVENTION

The present invention pertains generally to systems and methods for evaluating and monitoring a patient's heart muscle function. In particular, the present invention pertains to systems and methods that employ an extracorporeal sensor positioned on the patient to dynamically measure an arterial pressure in real time in order to identify a pressure/time rate-change (dp/dt) in arterial pressure. The present invention is particularly, but not exclusively, useful for evaluating dp/dt as an indicator of ventricular contractility and the health of the patient's heart muscle.

BACKGROUND OF THE INVENTION

For many reasons it may be clinically desirable to monitor and evaluate a patient's heart muscle function. A specific concern for such an evaluation is the heart's ability to properly pump blood into the patient's cardiovascular system. This leads to a consideration of the motive force that provides the heart's pumping function, which involves the heart's left ventricle. Thus, for the purpose of evaluating the heart's pumping action, the contractility of the left ventricle is a heart muscle function of specific interest.

From an anatomical perspective, it is well known that a healthy heart's left ventricle will contract during each cardiac cycle, and that the result is an immediate increase in blood pressure in the cardiovascular system. From a physical perspective it is recognized that the rate at which blood pressure increases in response to a ventricular contraction is a measure of heart function efficacy. Thus, an ability to identify a pressure/time rate-change in arterial pressure during a cardiac cycle (mathematically expressed as dp/dt) can be beneficial.

An important consideration for identifying dp/dt concerns how best to sense this rate of pressure change. For this purpose, several possibilities can be considered. In any event, it is important to use a blood pressure sensor that is minimally invasive, is accurate, does not interfere with other clinical operations, and is easily employed.

In clinical situations where it has been determined that the ventricular contractility of a patient's heart has become impaired by disease or damage, it is important to ascertain whether the heart muscle function can be somehow improved and monitored. One typical solution is to provide the patient with a new drug or an electrical pacemaker (biventricular pacing).

As is well known, the use of an electrical pacemaker for improving a heart muscle function requires the placement of electrodes at locations where they can be most effective. Depending on the clinical objective, the location for electrode placement may be limited to certain specific areas on the heart muscle. As a practical matter, without monitoring heart function as pacing is introduced, the proper placement of an electrode can be problematic.

In light of the above, it is an object of the present invention to provide a system for monitoring ventricular contractility which can be used to evaluate and improve a patient's heart muscle function. Another object of the present invention is to employ an extracorporeal pressure sensor for monitoring the rate of a blood pressure change during a ventricular contraction to indicate whether ventricular contractility is acceptable. Yet another object of the present invention is to provide a system for monitoring ventricular contractility that is easy to use, is accurate for its intended purpose and is comparatively cost effective.

SUMMARY OF THE INVENTION

A system for monitoring the ventricular contractility of a heart muscle is disclosed for the purposes of evaluating and improving a patient's heart muscle function. Included in the system is an extracorporeal pressure sensor that is positioned on the body of the patient to dynamically measure an arterial pressure. Specifically, the pressure sensor is used to identify a pressure/time rate-change in arterial pressure (dp/dt) within the time duration of a ventricular contraction during a cardiac cycle.

Also included is a device, such as a biventricular pacemaker, which can be used to electrically stimulate the patient's heart muscle function, and thereby energize its ventricular contractility. To do this, the stimulating device will have an electrode that is adapted to be placed on the epicardial surface of the patient's heart. As envisioned for the present invention, the electrode will be activated in accordance with a predetermined protocol which preferably requires at least one electric pulse from the electrode during each cardiac cycle of the heart muscle function. Moreover, the electrode can be moved between different, preselected locations on the heart's epicardial surface. Specifically, by moving the electrode, the system of the present invention can monitor ventricular contractibility as a function of electrode placement.

For an operation of the present invention, a monitor is connected to the extracorporeal pressure sensor. With this connection, pressure measurements for each stimulated ventricular contractility can be taken by the pressure sensor at each location and recorded. A timer connected with the monitor establishes a temporal reference for each of the pressure measurements. Thus, time referenced pressure measurements can provide a pressure/time rate change, expressed mathematically as dp/dt for each ventricular contraction. As recognized by the present invention, higher dp/dt values indicate a better heart muscle function.

As an added feature, the monitor can also include a patient-specific benchmark for determining an acceptable range for dp/dt for each pressure measurement. Thus, along with an evaluation of heart muscle function, the value of dp/dt also indicates whether the placement of the electrode is effective for stimulating the patient's heart muscle function. Preferably, the patient-specific benchmark will be based on i) the patient's medical history, ii) his/her present condition, and iii) his/her current symptoms.

In summary, the record created for the present invention can be evaluated to test the efficacy of electrode placement. The record can also be used to clinically evaluate the resultant response of the patient's heart muscle function. If desired, the response record can be presented on a visual display.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
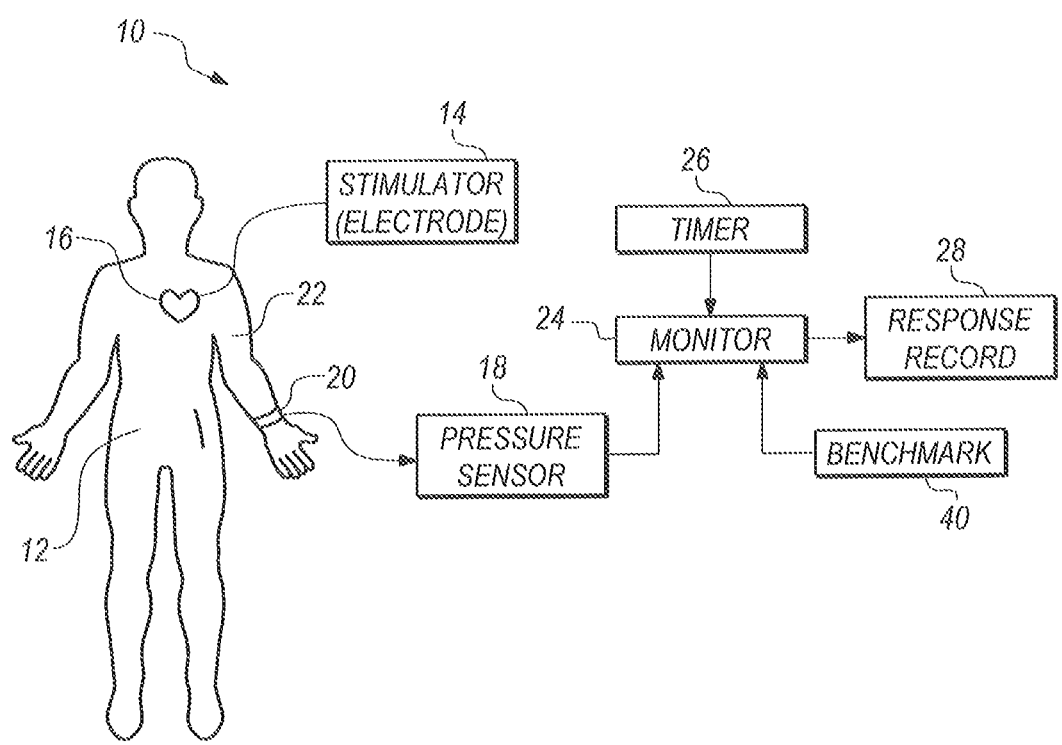
FIG. 1 is a schematic drawing of a heart function monitoring system in accordance with the present invention.

Referring initially to FIG. 1, a heart function monitoring system in accordance with the present invention is shown and is generally designated 10. As shown, the system 10 is connected with a patient 12 via two separate connection pathways. For one of these connections, an electrode (not shown) of a stimulator 14 is positioned relative to the heart muscle 16 of the patient 12 to stimulate contractions of the left ventricle of the heart muscle 16. For the other connection, a pressure sensor 18 is connected with the patient 12 via a pressure cuff 20 that is positioned on an arm 22 of the patient 12 to measure blood pressure.

It is to be appreciated that the disclosure here for the connection of the pressure sensor 18 to an arm 22 of the patient 12 is only exemplary. It will be appreciated that such a connection with the patient 12 is appropriate at any peripheral location where blood pressure readings can be made. For purposes of the present invention, both the stimulator 14 and the pressure sensor 18 are each of a type that is well known in the medical field. For example, the pressure sensor 18 may be an oximeter.

As envisioned for the present invention, the electrode of stimulator 14 is adapted to be placed and moved between different locations on an epicardial surface of the heart muscle 16 of the patient 12. Preferably, the electrode is placed at locations in the vicinity of (i.e. adjacent) a sympathetic nerve. The stimulator 14 is then operated in accordance with a predetermined protocol that requires at least one electric pulse from the electrode during each cardiac cycle of the heart muscle 16.

As the stimulator 14 is operated to stimulate a ventricular contraction of the heart muscle 16, its efficacy at each of several different locations is determined. In accordance with the present invention, an optimal electrode placement is determined by comparing the various responses obtained by the pressure sensor 18 as the electrode is moved over the epicardial surface of the heart muscle 16. As mentioned above, and disclosed in greater detail below, an optimal placement of the electrode is indicated when the value of dp/dt is maximized.

In FIG. 1 it will be seen that the system 10 includes a monitor 24. Also included is a timer 26 which is connected with the monitor 24 to provide a time input to the monitor 24. With input from both the timer 26 and the pressure sensor 18, the monitor 24 identifies a pressure/time rate-change (dp/dt) in the blood pressure of the patient 12 during each cardiac cycle. A record of the changes in blood pressure during a cardiac cycle can be created as a response record 28. Specifically, the pressure/time rate-change (dp/dt) of interest for the present invention occurs during the refractory period of the heart muscle 16 at the beginning of a contraction of the left ventricle.

Figure 2:
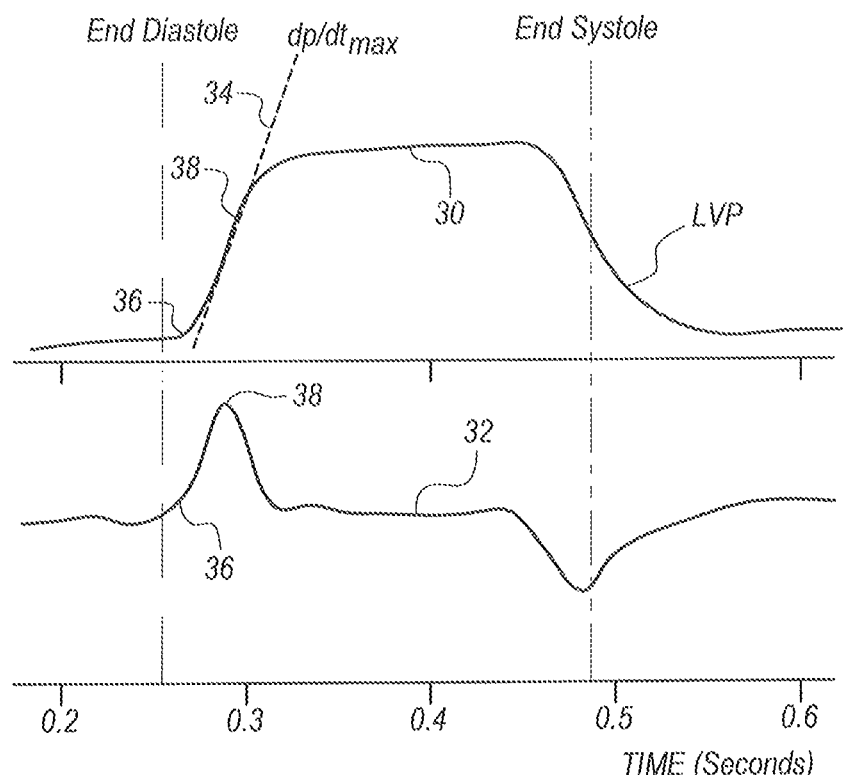
FIG. 2 is a left ventricle pressure tracing which shows the pressure/time variable dp/dt during a contraction of the left ventricle in a cardiac cycle of the heart muscle function.

FIG. 2 provides graphs for a typical left ventricle pressure tracing that are pertinent to the pressures generated by the left ventricle during systole. These graphs are provided here for purposes of disclosure. The upper part of FIG. 2 shows a graph of variations in the contraction pressure 30 that are generated in the left ventricle of the heart muscle 16 during systole in a cardiac cycle. In the lower part of FIG. 2, a graph is provided of the pressure/time rate change (dp/dt) 32 for the contraction pressure 30 that is shown in the upper part of FIG. 2.

Figure 3:
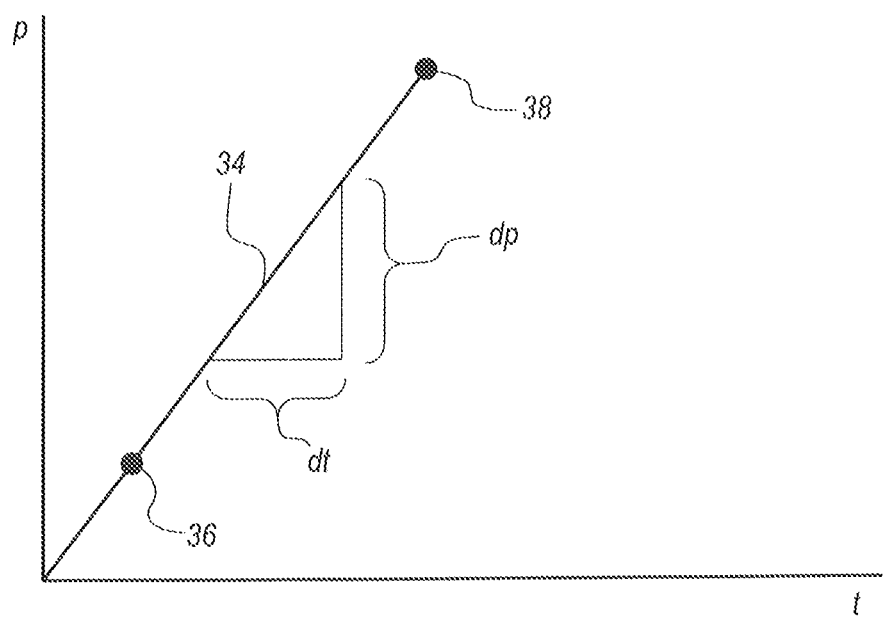
FIG. 3 is a line graph showing the mathematical characteristics of a pressure/time ($\Delta p/\Delta t$) relationship for evaluating a pressure tracing as shown in FIG. 2.

In FIG. 2, a pressure acceleration line 34 graphically shows the pressure/time rate change dp/dt 32 at which the contraction pressure 30 initially rises during a contraction of the left ventricle. Mathematically, it is the dp/dt 32 between points 36 and 38 that is of particular importance for the present invention. FIG. 3 shows a more detailed relationship between the slope dp/dt 32 of the pressure acceleration line 34, and the effect a change in pressure $\Delta p$ can have during a time interval $\Delta t$. The import here is that as $\Delta p$ increases or decreases, the value of slope dp/dt 32 will correspondingly increase and decrease. Moreover, changes in dp/dt 32 will change the orientation of the pressure acceleration line 34. As recognized by the present invention, the use of an extracorporeal pressure sensor 18 can detect changes in dp/dt 32, which can then be used to evaluate the ventricular contractility.

For clinical purposes, a patient-specific benchmark 40 can be established for determining an acceptable range for dp/dt. Accordingly, a value for dp/dt that is determined to be in the acceptable range indicates an effective placement of the electrode for stimulating the patient's heart muscle function. As envisioned for the present invention, the patient-specific benchmark 40 will typically be based on i) a patient's medical history, ii) the patient's present condition, and iii) his/her current symptoms. In any event, a response record 28 can be created for use in clinically evaluating the heart muscle 16, and the response record 28 can be presented on a visual display (not shown) during placement of the electrode.

While the particular System and Method for Indirect Measurement of Ventricular Contractility as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for monitoring ventricular contractility to evaluate and improve a patient's heart muscle function, which comprises:
    a device for electrically stimulating ventricular contractility, wherein the device includes an electrode adapted to be placed and moved between different preselected locations on an epicardial surface of the heart muscle of the patient, to stimulate a ventricular contraction of the heart muscle in accordance with a predetermined protocol;
    an extracorporeal pressure sensor positioned on the body of the patient for dynamically measuring an arterial pressure influenced by the stimulated ventricular contraction;
    a monitor connected to the extracorporeal pressure sensor for creating a pressure response record of the stimulated ventricular contractility; and
    a timer connected with the monitor to establish a temporal reference for the pressure response record, to identify a pressure/time rate-change in arterial pressure (dp/dt), wherein dp/dt is measured within a time duration of a ventricular contraction during a cardiac cycle at each of the preselected locations to test the efficacy of electrode placement and to evaluate the patient's heart muscle function.

2. The system of claim 1 wherein the device for electrically stimulating a ventricular contraction is a pacemaker.

3. The system of claim 1 wherein the electrode of the device for electrically stimulating a ventricular contraction is positioned on the epicardial surface adjacent a sympathetic nerve.

4. The system of claim 1 wherein the predetermined protocol requires at least one electric pulse from the electrode during each cardiac cycle of the heart muscle function.

5. The system of claim 1 wherein the extracorporeal pressure sensor is positioned on an arm of the patient and is an oximeter.

6. The system of claim 1 further comprising a patient-specific benchmark for determining an acceptable range for dp/dt, wherein a value for dp/dt in the acceptable range indicates an effective placement of the electrode for stimulating the patient's heart muscle function, and wherein the patient-specific benchmark is based on i) a patient's medical history, ii) the patient's present condition, and iii) his/her current symptoms.

7. The system of claim 1 further comprising a response record created by the monitor for use in clinically evaluating the heart muscle function wherein the response record is presented on a visual display.

8. A system for monitoring ventricular contractility to evaluate and improve a patient's heart muscle function, which comprises:
   an extracorporeal pressure sensor positioned on the body of the patient for dynamically measuring an arterial pressure;
   a monitor connected to the extracorporeal pressure sensor for creating a pressure response record of the monitored ventricular contractility; and
   a timer connected with the monitor to establish a temporal reference for the pressure response record, to identify a pressure/time rate-change in arterial pressure (dp/dt), wherein dp/dt is measured within a time duration of a ventricular contraction during a cardiac cycle to test the efficacy of a stimulation electrode placement and to evaluate the patient's heart muscle function.

9. The system of claim 8 further comprising:
   a device for electrically stimulating ventricular contractility, wherein the device includes an electrode adapted to be placed and moved between different preselected locations on an epicardial surface of the heart muscle of the patient, to stimulate a ventricular contraction of the heart muscle in accordance with a predetermined protocol; and
   a patient-specific benchmark for determining an acceptable range for dp/dt, wherein a value for dp/dt in the acceptable range indicates an effective placement of the electrode for stimulating the patient's heart muscle function.

10. The system of claim 8 wherein the electrode of the device is positioned adjacent a sympathetic nerve, wherein the extracorporeal pressure sensor is positioned on an arm of the patient, and wherein the predetermined protocol requires at least one electric pulse from the electrode during each cardiac cycle of the heart muscle function.

11. A method for evaluating a ventricular contractility of a patient's heart muscle function which comprises the steps of:
   placing an electrode on an epicardial surface of the heart muscle of the patient, to stimulate a ventricular contraction of the heart muscle in accordance with a predetermined protocol;
   positioning an extracorporeal pressure sensor on the body of the patient for dynamically measuring an arterial pressure influenced by the stimulated ventricular contraction;
   creating a pressure response record of the stimulated ventricular contractility; and
   identifying a temporal reference for the pressure response record to present a pressure/time rate-change in arterial pressure (dp/dt), wherein dp/dt is measured within a time duration of a ventricular contraction during a cardiac cycle to test the efficacy of electrode placement and to evaluate the patient's heart muscle function.

12. The method of claim 11 wherein the placing step is accomplished by placing the electrode adjacent a sympathetic nerve.

13. The method of claim 11 further comprising the step of determining an acceptable range for dp/dt, wherein a value for dp/dt in the acceptable range indicates an effective placement of the electrode for stimulating the patient's heart muscle function.

14. The method of claim 11 wherein the positioning step is accomplished by locating the extracorporeal pressure sensor on an arm of the patient.

15. The method of claim 11 wherein the predetermined protocol requires at least one electric pulse from the electrode during each cardiac cycle of the heart muscle function.

* * * * *